United States Patent [19]
Lichy et al.

[11] Patent Number: 5,491,064
[45] Date of Patent: Feb. 13, 1996

[54] HTS-1 GENE, A HUMAN TUMOR SUPPRESSOR GENE

[75] Inventors: Jack H. Lichy, Silver Spring; Peter M. Howley, Potomac, both of Md.

[73] Assignee: The United States of America as represented by the Department of Health and Human Services, Washington, D.C.

[21] Appl. No.: 369,043

[22] Filed: Jan. 5, 1995

Related U.S. Application Data

[63] Continuation of Ser. No. 916,762, Jul. 17, 1992, abandoned.
[51] Int. Cl.$^6$ .............................. C12Q 1/68; C07H 21/04
[52] U.S. Cl. .................................................. 435/6; 536/23.1
[58] Field of Search ...................... 435/6, 320.1; 935/78; 536/23.1; 436/64, 813

[56] References Cited

PUBLICATIONS

Braaten et al., Nucleic Acid Res, 16(3):865–881 (1988) "Locations and contexts of sequences that hybridize . . . ".
Zappavigna et al., EMBO. J., 10:4177–4187 (1991) "HOX 4 genes encode transcription factors . . . ".
Dixon et al., Proc. Natl. Acad. Sci. U.S.A. (1988) 85:416–420, "Cloning of the cDNA for human . . . ".
Modi et al., Cytogen. Cell. Genetics, 58(N3-4):1968 (1991) "HTS—A gene associated . . . ".
Stanbridge, E. J., "Suppression of Malignancy in Human Cells," Nature 260:17–20 (1976).
Kaelbling, M. and Klinger, H. P., "Suppression of Tumorigenicity in Somatic Cell Hybrids III. Cosegregation of Human Chromosome 11 of a Normal Cell and Suppression of Tumorigenicity in Intraspecies Hybrids of Normal Diploid X Malignant Cells," Cytogenet. Cell Genet. 42:65–70 (1986).
Klinger, H. P., "Suppression of Tumorigenicity in Somatic Cell Hybrids I. Suppression and Reexpression of Tumorigenicity in Diploid HumanXD98AH2 Hybrids and Independent Segregation of Tumorigenicity from Other Cell Phenotypes," Cytogenet. Cell Genet. 27:254–266 (1980).
Stanbridge, E. J., et al., "Human Cell Hybrids: Analysis of Transformation and Tumorigenicity," Science 215:252–259 (1982).
Junien, C., et al., "Report of the Second Chromosome 11 Workshop," Genomics 12:620–625 (1992).
Koi, M., et al., "Normal Human Chromosome 11 Suppresses Tumorigenicity of Human Cervical Tumor Cell Line SiHa," Mol. Carcinogen. 2:12–21 (1989).
Oshimura, M., et al., "Transfer of a Normal Human Chromosome 11 Suppresses Tumorigenicity of Some but Not All Tumor Cell Lines," J. Cell. Biochem. 42:135–142 (1990).
Latham, K. M. and Stanbridge, E. J., "Examination of the Oncogenic Potential of a Tumor–associated Antigen, Intestinal Alkaline Phosphatase, in HeLa X Fibroblast Cell Hybrids," Cancer Res. 52:616–622 (1992).
Dowdy, S. F., et al., "The Isolation and Characterization of a Novel cDNA Demonstrating an Altered mRNA Level in Nontumorigenic Wilms' Microcell Hybrid Cells," Nuc. Acids Res. 19:5763–5769 (1991).
Weissmann, B. E., et al., "Introduction of a Normal Human Chromosome 11 into a Wilms' Tumor Cell Line Controls Its Tumorigenic Expression," Science 236:175–180 (1987).
Srivatsan, E. S., et al., "Implication of Chromosome 11 in the Suppression of Neoplastic Expression in Human Cell Hybrids," Cancer Res. 46:6174–6179 (1986).
Saxon, P. J., et al., "Introduction of Human Chromosome 11 Via Microcell Transfer Controls Tumorigenic Expression of HeLa Cells," EMBO J. 5:3461–3466 (1986).
Latham, K. M., and Stanbridge, E. J., "Identification of the HeLa Tumor–associated Antigen, p75/150, as Intestinal Alkaline Phosphatase and Evidence for Its Transcriptional Regulation," Proc. Natl. Acad. Sci. USA 87:1263–1267 (1990).

Primary Examiner—W. Gary Jones
Assistant Examiner—Eggerton Campbell
Attorney, Agent, or Firm—Townsend and Townsend and Crew

[57] ABSTRACT

A gene which is associated with tumor suppression and is localized on chromosome 11 has now been identified. The identification, localization and sequence of a gene which demonstrates differential expression in a manner that correlates with tumorigenicity suggests that this gene could potentially be used for gene therapy in cancers deleted or altered in their expression of the gene. Furthermore, a gene which is localized on chromosome 11p15, with identified polymorphisms, could be used for analysis of tumor DNA for loss of heterozygosity at chromosome 11p15. This region of chromosome 11 shows frequent loss of heterozygosity (LOH) in many human malignancies. Thus, the determination of LOH at chromosome 11p15 may be useful in predicting the prognosis of that tumor.

22 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 4406 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 244..3655

( x i ) SEQUENCE DESCRIPTION: SEQ ID NO:1:

```
CTGCAGGAGC GGCTCCTCCT CCGGGCCGCG CGGCTCCCGG CGAGACCCCA TCCAGGCGCC        60

GCGCCCGGCC CGGCTGGGGA ACGCAGAGAT TTCACACCCT TTGGAGAGTT TCTTTCTTGG       120

ATAATTCAGG AAGATGAGAG ACTGCTTAGG CGCCACCACT AGTACCATGA GTCCCTGCAC       180

TGGTTAAAGC CATCGCCACA ACCTGGACAG GCAGCAAGGG CTCTGGGTTT GCAGAGAGCC       240

GAA ATG ACC ATG ACT GCC AAC AAG AAT TCC AGC ATC ACC CAC GGA GCT        288
    Met Thr Met Thr Ala Asn Lys Asn Ser Ser Ile Thr His Gly Ala
    1               5                   10                  15

GGT GGC ACT AAA GCC CCT CGG GGG ACT CTG AGC AGG TCT CAG TCA GTC        336
Gly Gly Thr Lys Ala Pro Arg Gly Thr Leu Ser Arg Ser Gln Ser Val
                20                  25                  30

TCT CCA CCT CCA GTC CTC TCC CCA CCA AGG AGT CCC ATC TAC CCG CTC        384
Ser Pro Pro Pro Val Leu Ser Pro Pro Arg Ser Pro Ile Tyr Pro Leu
                35                  40                  45

AGT GAT AGT GAA ACC TCA GCC TGC AGG TAC CCC AGC CAC TCC AGC TCC        432
Ser Asp Ser Glu Thr Ser Ala Cys Arg Tyr Pro Ser His Ser Ser Ser
                50                  55                  60

CGG GTG CTC CTC AAG GAC CGG CAC CCC CCA GCT CCT TCA CCC CAG AAT        480
Arg Val Leu Leu Lys Asp Arg His Pro Pro Ala Pro Ser Pro Gln Asn
        65                  70                  75.

CCT CAA GAT CCC TCC CCA GAT ACT TCC CCA CCC ACC TGT CCC TTC AAG        528
Pro Gln Asp Pro Ser Pro Asp Thr Ser Pro Pro Thr Cys Pro Phe Lys
80                  85                  90                  95

ACC GCC AGC TTC GGT TAT TTG GAC AGA AGC CCT TCG GCG TGC AAG AGA        576
Thr Ala Ser Phe Gly Tyr Leu Asp Arg Ser Pro Ser Ala Cys Lys Arg
                100                 105                 110

GAC ACC CAA AAG GAA AGT GTC CAA GGC GCA GCC CAG GAT GTA GCA GGG        624
Asp Thr Gln Lys Glu Ser Val Gln Gly Ala Ala Gln Asp Val Ala Gly
                115                 120                 125

GTC GCT GCC TGC CTC CCC CTT GCC CAG AGC ACG CCA TTC CCG GGG CCA        672
Val Ala Ala Cys Leu Pro Leu Ala Gln Ser Thr Pro Phe Pro Gly Pro
            130                 135                 140

GCA GCT GGC CCC CGG GGC GTC TTG CTG ACC CGT ACC GGT ACC CGC AGC        720
Ala Ala Gly Pro Arg Gly Val Leu Leu Thr Arg Thr Gly Thr Arg Ser
Ala Ala Gly Pro Arg Gly Val Leu Leu Thr Arg Thr Gly Thr Arg Ser
            145                 150                 155

CCA CAG CCT GGG CAT CCG GGA GAA GAT ATA GCA TGG GAA GGT CGC CGA        768
Pro Gln Pro Gly His Pro Gly Glu Asp Ile Ala Trp Glu Gly Arg Arg
160                 165                 170                 175

GAG GCG TCG CCC AGG ATG AGC ATG TGT GGA GAG AAG CGG GAG GGC TCT        816
Glu Ala Ser Pro Arg Met Ser Met Cys Gly Glu Lys Arg Glu Gly Ser
                180                 185                 190
```

| | | | | | | | | | | | | | | | | |
|---|---|---|---|---|---|---|---|---|---|---|---|---|---|---|---|---|
| GGG | AGC | GAG | TGG | GCG | GCC | AGT | GAG | GGC | TGC | CCC | AGC | CTG | GGC | TGT | CCC | 864 |
| Gly | Ser | Glu | Trp<br>195 | Ala | Ala | Ser | Glu | Gly<br>200 | Cys | Pro | Ser | Leu | Gly<br>205 | Cys | Pro | |
| AGC | GTG | GTG | CCG | TCC | CCC | TGC | AGC | TCT | GAA | AAG | ACC | TTT | GAT | TTC | AAG | 912 |
| Ser | Val | Val<br>210 | Pro | Ser | Pro | Cys | Ser<br>215 | Ser | Glu | Lys | Thr | Phe<br>220 | Asp | Phe | Lys | |
| GGC | CTC | CGG | AGG | ATG | AGC | AGG | ACC | TTC | TCC | GAG | TGT | TCC | TAC | CCA | GAG | 960 |
| Gly | Leu<br>225 | Arg | Arg | Met | Ser | Arg<br>230 | Thr | Phe | Ser | Glu | Cys<br>235 | Ser | Tyr | Pro | Glu | |
| ACT | GAG | GAG | GAG | GGA | GAG | GCG | CTC | CCT | GTC | CGG | GAC | TCT | TTC | TAC | CGG | 1008 |
| Thr<br>240 | Glu | Glu | Glu | Gly<br>245 | Glu | Ala | Leu | Pro | Val<br>250 | Arg | Asp | Ser | Phe | Tyr<br>255 | Arg | |
| CTG | GAG | AAA | CGG | CTG | GGC | CGG | AGT | GAG | CCC | AGC | GCC | TTC | CTC | AGG | GGG | 1056 |
| Leu | Glu | Lys | Arg | Leu<br>260 | Gly | Arg | Ser | Glu | Pro<br>265 | Ser | Ala | Phe | Leu | Arg<br>270 | Gly | |
| CAT | GGC | AGC | AGG | AAG | GAG | AGC | TCA | GCA | GTG | CTG | AGC | CGG | ATC | CAG | AAA | 1104 |
| His | Gly | Ser | Arg<br>275 | Lys | Glu | Ser | Ser | Ala<br>280 | Val | Leu | Ser | Arg | Ile<br>285 | Gln | Lys | |
| ATT | GAA | CAG | GTC | CTG | AAG | GAG | CAG | CCG | GGC | CGG | GGG | CTC | CCC | CAG | CTC | 1152 |
| Ile | Glu | Gln<br>290 | Val | Leu | Lys | Glu | Gln<br>295 | Pro | Gly | Arg | Gly | Leu<br>300 | Pro | Gln | Leu | |
| CCC | AGC | AGC | TGC | TAC | AGC | GTC | GAC | CGG | GGG | AAA | AGG | AAG | ACT | GGA | ACC | 1200 |
| Pro | Ser<br>305 | Ser | Cys | Tyr | Ser | Val<br>310 | Asp | Arg | Gly | Lys | Arg<br>315 | Lys | Thr | Gly | Thr | |
| TTG | GGC | TCC | TTG | GAG | GAG | CCG | GCA | GGG | GGC | GCG | AGT | GTG | AGC | GCT | GGC | 1248 |
| Leu<br>320 | Gly | Ser | Leu | Glu | Glu<br>325 | Pro | Ala | Gly | Gly | Ala<br>330 | Ser | Val | Ser | Ala | Gly<br>335 | |
| AGC | CGG | GCA | GTC | GGA | GTG | GCT | GGT | GTT | GCG | GGG | GAG | GCG | GGC | CCA | CCC | 1296 |
| Ser | Arg | Ala | Val | Gly<br>340 | Val | Ala | Gly | Val | Ala<br>345 | Gly | Glu | Ala | Gly | Pro<br>350 | Pro | |
| CCA | GAG | AGG | GAA | GGC | AGT | GGT | TCC | ACT | AAG | CCC | GGG | ACC | CCT | GGA | AAT | 1344 |
| Pro | Glu | Arg | Glu<br>355 | Gly | Ser | Gly | Ser | Thr<br>360 | Lys | Pro | Gly | Thr | Pro<br>365 | Gly | Asn | |
| AGC | CCT | AGC | TCC | CAG | CGG | CTG | CCA | TCG | AAG | AGT | TCC | CTC | GAT | CCC | GCT | 1392 |
| Ser | Pro | Ser<br>370 | Ser | Gln | Arg | Leu | Pro<br>375 | Ser | Lys | Ser | Ser | Leu<br>380 | Asp | Pro | Ala | |
| GTG | AAC | CCT | GTC | CCC | AAA | CCC | AAG | CGC | ACC | TTT | GAA | TAC | GAG | GCT | GAG | 1440 |
| Val | Asn<br>385 | Pro | Val | Pro | Lys | Pro<br>390 | Lys | Arg | Thr | Phe | Glu<br>395 | Tyr | Glu | Ala | Glu | |
| AAG | AAC | CCC | AAG | AGT | AAG | CCC | AGT | AAT | GGT | CTA | CCT | CCT | TCA | CCC | ACA | 1488 |
| Lys<br>400 | Asn | Pro | Lys | Ser | Lys<br>405 | Pro | Ser | Asn | Gly | Leu<br>410 | Pro | Pro | Ser | Pro | Thr<br>415 | |
| CCT | GCT | GCT | CCA | CCT | CCC | TTG | CCC | TCC | ACC | CCA | GCC | CCG | CCA | GTC | ACC | 1536 |
| Pro | Ala | Ala | Pro<br>420 | Pro | Pro | Leu | Pro | Ser<br>425 | Thr | Pro | Ala | Pro | Pro<br>430 | Val | Thr | |
| CGG | AGA | CCC | AAG | AAG | GAC | ATG | CGT | GGT | CAC | CGC | AAG | TCC | CAG | AGC | AGA | 1584 |
| Arg | Arg | Pro | Lys<br>435 | Lys | Asp | Met | Arg | Gly<br>440 | His | Arg | Lys | Ser | Gln<br>445 | Ser | Arg | |
| AAA | TCC | TTT | GAG | TTT | GAG | GAT | GCA | TCC | AGT | CTC | CAG | TCC | CTG | TAC | CCC | 1632 |
| Lys | Ser | Phe<br>450 | Glu | Phe | Glu | Asp | Ala<br>455 | Ser | Ser | Leu | Gln | Ser<br>460 | Leu | Tyr | Pro | |
| TCT | TCT | CCC | ACT | GAG | AAT | GGT | ACT | GAG | AAC | CAA | CCC | AAG | TTT | GGA | TCC | 1680 |
| Ser | Ser<br>465 | Pro | Thr | Glu | Asn | Gly<br>470 | Thr | Glu | Asn | Gln | Pro<br>475 | Lys | Phe | Gly | Ser | |
| AAA | AGC | ACT | TTA | GAA | GAA | AAT | GCC | TAT | GAA | GAT | ATT | GTG | GGA | GAT | CTG | 1728 |
| Lys<br>480 | Ser | Thr | Leu | Glu | Glu<br>485 | Asn | Ala | Tyr | Glu | Asp<br>490 | Ile | Val | Gly | Asp<br>495 | Leu | |
| CCC | AAG | GAG | AAT | CCA | TAT | GAG | GAT | GTG | GAC | TTA | AAG | AGC | CGA | AGA | GCA | 1776 |
| Pro | Lys | Glu | Asn | Pro<br>500 | Tyr | Glu | Asp | Val | Asp<br>505 | Leu | Lys | Ser | Arg | Arg<br>510 | Ala | |

```
GGA CGA AAA TCC CAG CAA CTG TCT GAG AAC TCC TTG GAC TCT TTG CAC    1824
Gly Arg Lys Ser Gln Gln Leu Ser Glu Asn Ser Leu Asp Ser Leu His
            515             520             525

AGG ATG TGG AGT CCT CAG GAC AGG AAG TAC AAC AGC CCG CCC ACA CAG    1872
Arg Met Trp Ser Pro Gln Asp Arg Lys Tyr Asn Ser Pro Pro Thr Gln
            530             535             540

CTT TCC CTG AAA CCC AAC AGC CAG TCC CTG CGC AGT GGG AAC TGG TCA    1920
Leu Ser Leu Lys Pro Asn Ser Gln Ser Leu Arg Ser Gly Asn Trp Ser
            545             550             555

GAA AGG AAG AGC CAC CGG CTG CCA CGA TTA CCC AAG AGG CAC AGC CAT    1968
Glu Arg Lys Ser His Arg Leu Pro Arg Leu Pro Lys Arg His Ser His
560             565             570             575

GAC GAC ATG CTG CTG CTG GCT CAG CTG AGT CTG CCG TCC TCA CCC TCC    2016
Asp Asp Met Leu Leu Leu Ala Gln Leu Ser Leu Pro Ser Ser Pro Ser
            580             585             590

AGC CTC AAT GAA GAC AGC CTC AGC ACC ACC AGC GAG CTG CTG TCC AGC    2064
Ser Leu Asn Glu Asp Ser Leu Ser Thr Thr Ser Glu Leu Leu Ser Ser
            595             600             605

CGC CGG GCC CGC CGC ATT CCC AAG CTT GTC CAA AGA ATT AAC TCC ATC    2112
Arg Arg Ala Arg Arg Ile Pro Lys Leu Val Gln Arg Ile Asn Ser Ile
            610             615             620

TAC AAT GCC AAG AGA GGA AAG AAG AGA TTA AAA AAG TTG TCT ATG TCC    2160
Tyr Asn Ala Lys Arg Gly Lys Lys Arg Leu Lys Lys Leu Ser Met Ser
            625             630             635

AGC ATT GAA ACA GCA TCA CTG AGA GAT GAA AAC AGT GAG AGC GAG AGC    2208
Ser Ile Glu Thr Ala Ser Leu Arg Asp Glu Asn Ser Glu Ser Glu Ser
640             645             650             655

GAC TCT GAT GAC AGG TTC AAA GCC CAC ACA CAG CGC CTG GTC CAC ATC    2256
Asp Ser Asp Asp Arg Phe Lys Ala His Thr Gln Arg Leu Val His Ile
            660             665             670

CAG TCG ATG CTG AAG CGC GCC CCC AGC TAT CGC ACG CTG GAG CTG GAG    2304
Gln Ser Met Leu Lys Arg Ala Pro Ser Tyr Arg Thr Leu Glu Leu Glu
            675             680             685

CTG CTG GAG TGG CAG GAG CGG GAG CTT TTT GAG TAC TTT GTG GTG GTG    2352
Leu Leu Glu Trp Gln Glu Arg Glu Leu Phe Glu Tyr Phe Val Val Val
            690             695             700

TCC CTC AAG AAG AAG CCA TCG CGA AAC ACC TAC CTC CCC GAA GTC TCC    2400
Ser Leu Lys Lys Lys Pro Ser Arg Asn Thr Tyr Leu Pro Glu Val Ser
705             710             715

TAC CAG TTT CCC AAG CTG GAC CGA CCC ACC AAG CAG ATG CGA GAG GCA    2448
Tyr Gln Phe Pro Lys Leu Asp Arg Pro Thr Lys Gln Met Arg Glu Ala
720             725             730             735

GAG GAA AGG CTC AAA GCC ATT CCC CAG TTT TGC TTC CCT GAT GCC AAG    2496
Glu Glu Arg Leu Lys Ala Ile Pro Gln Phe Cys Phe Pro Asp Ala Lys
            740             745             750

GAC TGG CTT CCT GTG TCA GAG TAT AGC AGT GAG ACC TTT TCT TTC ATG    2544
Asp Trp Leu Pro Val Ser Glu Tyr Ser Ser Glu Thr Phe Ser Phe Met
            755             760             765

CTG ACT GGG GAA GAT GGC AGC AGA CGC TTT GGC TAC TGC AGG CGC TTA    2592
Leu Thr Gly Glu Asp Gly Ser Arg Arg Phe Gly Tyr Cys Arg Arg Leu
            770             775             780

CTG CCA AGT GGG AAA GGG CCC CGG TTG CCA GAG GTG TAC TGT GTC ATC    2640
Leu Pro Ser Gly Lys Gly Pro Arg Leu Pro Glu Val Tyr Cys Val Ile
            785             790             795

AGC CGC CTT GGC TGC TTC GGC TTG TTT TCC AAG GTC CTA GAT GAG GTG    2688
Ser Arg Leu Gly Cys Phe Gly Leu Phe Ser Lys Val Leu Asp Glu Val
800             805             810             815

GAG CGC CGG CGT GGG ATC TCC GCT GCA TTG GTC TAT CCT TTC ATG AGA    2736
Glu Arg Arg Arg Gly Ile Ser Ala Ala Leu Val Tyr Pro Phe Met Arg
            820             825             830
```

```
AGT CTC ATG GAG TCG CCC TTC CCA GCC CCA GGG AAG ACC ATC AAA GTG        2784
Ser Leu Met Glu Ser Pro Phe Pro Ala Pro Gly Lys Thr Ile Lys Val
            835             840             845

AAG ACA TTC CTG CCA GGT GCT GGC AAT GAG GTG TTA GAG CTG CGG CGG        2832
Lys Thr Phe Leu Pro Gly Ala Gly Asn Glu Val Leu Glu Leu Arg Arg
        850             855             860

CCC ATG GAC TCA AGG CTG GAG CAC GTG GAC TTT GAG TGC CTT TTT ACC        2880
Pro Met Asp Ser Arg Leu Glu His Val Asp Phe Glu Cys Leu Phe Thr
        865             870             875

TGC CTC AGT GTG CGC CAG CTC ATC CGA ATC TTT GCC TCA CTG CTG CTG        2928
Cys Leu Ser Val Arg Gln Leu Ile Arg Ile Phe Ala Ser Leu Leu Leu
880             885             890             895

GAG CGC CGG GTC ATT TTT GTG GCA GAT AAG CTC AGT ACC CTC TCC AGC        2976
Glu Arg Arg Val Ile Phe Val Ala Asp Lys Leu Ser Thr Leu Ser Ser
                900             905             910

TGC TCC CAC GCG GTG GTG GCC TTG CTC TAC CCC TTC TCC TGG CAG CAC        3024
Cys Ser His Ala Val Val Ala Leu Leu Tyr Pro Phe Ser Trp Gln His
            915             920             925

ACC TTC ATT CCT GTC CTC CCG GCC TCC ATG ATT GAC ATC GTC TGC TGT        3072
Thr Phe Ile Pro Val Leu Pro Ala Ser Met Ile Asp Ile Val Cys Cys
        930             935             940

CCC ACC CCC TTC CTG GTT GGC CTG CTC TCC AGC TCC CTC CCC AAA CTG    3120
    Pro Thr Pro Phe Leu Val Gly Leu Leu Ser Ser Ser Leu Pro Lys Leu
            945             950             955

AAG GAG CTG CCT GTG GAG GAG GCG CTG ATG GTG AAT CTG GGA TCT GAC        3168
Lys Glu Leu Pro Val Glu Glu Ala Leu Met Val Asn Leu Gly Ser Asp
960             965             970             975

CGA TTC ATC CGA CAG ATG GAC GAC GAA GAC ACG TTG TTA CCT AGG AAG        3216
Arg Phe Ile Arg Gln Met Asp Asp Glu Asp Thr Leu Leu Pro Arg Lys
            980             985             990

TTA CAG GCA GCT CTG GAG CAG GCT CTG GAG AGG AAG AAT GAG CTG ATC        3264
Leu Gln Ala Ala Leu Glu Gln Ala Leu Glu Arg Lys Asn Glu Leu Ile
        995             1000            1005

TCC CAG GAC TCT GAC AGC GAC TCC GAC GAT GAA TGT AAT ACC CTC AAT        3312
Ser Gln Asp Ser Asp Ser Asp Ser Asp Asp Glu Cys Asn Thr Leu Asn
        1010            1015            1020

GGG CTG GTG TCG GAG GTG TTT ATC CGG TTC TTT GTG GAG ACC GTT GGG        3360
Gly Leu Val Ser Glu Val Phe Ile Arg Phe Phe Val Glu Thr Val Gly
        1025            1030            1035

CAC TAC TCC CTC TTT CTG ACA CAG AGT GAG AAG GGA GAG AGG GCC TTT        3408
His Tyr Ser Leu Phe Leu Thr Gln Ser Glu Lys Gly Glu Arg Ala Phe
1040            1045            1050            1055

CAG CGA GAG GCC TTC CGC AAA TCT GTG GCC TCC AAA AGC ATC CGC CGC        3456
Gln Arg Glu Ala Phe Arg Lys Ser Val Ala Ser Lys Ser Ile Arg Arg
            1060            1065            1070

TTT CTT GAG GTT TTT ATG GAG TCT CAG ATG TTT GCT GGC TTC ATC CAA        3504
Phe Leu Glu Val Phe Met Glu Ser Gln Met Phe Ala Gly Phe Ile Gln
            1075            1080            1085

GAC AGG GAG CTA AGA AAG TGT CGG GCA AAG GGC CTT TTT GAG CAG CGA        3552
Asp Arg Glu Leu Arg Lys Cys Arg Ala Lys Gly Leu Phe Glu Gln Arg
            1090            1095            1100

GTG GAG CAG TAC TTA GAA GAA CTC CCA GAC ACT GAG CAG AGT GGA ATG        3600
Val Glu Gln Tyr Leu Glu Glu Leu Pro Asp Thr Glu Gln Ser Gly Met
        1105            1110            1115

AAT AAG TTT CTC CGA GGT TTG GGC AAC AAA ATG AAG TTT CTC CAC AAG        3648
Asn Lys Phe Leu Arg Gly Leu Gly Asn Lys Met Lys Phe Leu His Lys
1120            1125            1130            1135

AAG AAT T AAGCCTCCTT CTCAGTAGCA GAGTCCAGTG CCTTGCAGAG CCTGAAGCCT       3705
Lys Asn

GGGGAGAAGG CCCAGCCTGG GACCCTCTGG GCTGCTGTGG CTCCTCTGCC CCCACAGATC     3765
```

| | | | | |
|---|---|---|---|---|
| CTATCCTCCA | AGCCAGCCCA | CCTCTGCCTT | CATCATATCC | CAGGATACTG | TTTGTAAATA | 3825 |
| ATCTGCTGTA | AGCTTTCTTA | ACTGTTTTTT | GTAACAAGCA | AGAGAATAT | GGCAAATATT | 3885 |
| TGTATATTCC | CAAGGGGCCG | GGTGCTTTCC | TGTCCTGCCA | GAGCATGGAT | GAAGTTTCGC | 3945 |
| TGGGTGCTCG | TGACTGGCCA | GTTTTGTGCA | GCTGACTGTC | TCAGCCAAAC | CACTGATCTT | 4005 |
| CCCTGGAGGC | CTTCGGCCTG | CCTGCCTGCC | TGCCTGAGGT | CCCCGCTGCC | AGTCCCGGGC | 4065 |
| CCTGGAGAGC | AGATGCTGTC | TTGTTATGTA | CAGGAGGACC | TTTTAAAAAA | ATCAAGTTTC | 4125 |
| TATTTTTGC | TGGTAGTCCG | CATACCCATA | CCCTCTGTTT | TTGAAAGGCA | AAGGCCAATC | 4185 |
| AGTCCCCATT | TGTAGCATGG | CACCAGGGTC | TTAGGCCTAG | TCCTCTCATT | CCTCCCACCC | 4245 |
| TCCGAGATGG | TCAGTGTGTC | ATGGGAAGCC | CACCCCCAGC | TCTGCCAGTG | CTCTCTGGGC | 4305 |
| CTGGCTCCCA | GTCAGTGGTG | GCCACGATGC | GGTACAGGGC | ATCCCTCCTT | CCCATCTACG | 4365 |
| GGTGTTGTCA | ATAAACAATG | TACAGTTGTT | TGGGCCCAGA | G | | 4406 |

( 2 ) INFORMATION FOR SEQ ID NO:2:

( i ) SEQUENCE CHARACTERISTICS:
        ( A ) LENGTH: 1137 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Thr Met Thr Ala Asn Lys Asn Ser Ser Ile Thr His Gly Ala Gly
  1               5                  10                  15

Gly Thr Lys Ala Pro Arg Gly Thr Leu Ser Arg Ser Gln Ser Val Ser
             20                  25                  30

Pro Pro Pro Val Leu Ser Pro Pro Arg Ser Pro Ile Tyr Pro Leu Ser
         35                  40                  45

Asp Ser Glu Thr Ser Ala Cys Arg Tyr Pro Ser His Ser Ser Ser Arg
     50                  55                  60

Val Leu Leu Lys Asp Arg His Pro Ala Pro Ser Pro Gln Asn Pro
 65                  70                  75                  80

Gln Asp Pro Ser Pro Asp Thr Ser Pro Pro Thr Cys Pro Phe Lys Thr
                 85                  90                  95

Ala Ser Phe Gly Tyr Leu Asp Arg Ser Pro Ser Ala Cys Lys Arg Asp
            100                 105                 110

Thr Gln Lys Glu Ser Val Gln Gly Ala Ala Gln Asp Val Ala Gly Val
        115                 120                 125

Ala Ala Cys Leu Pro Leu Ala Gln Ser Thr Pro Phe Pro Gly Pro Ala
130                 135                 140

Ala Gly Pro Arg Gly Val Leu Leu Thr Arg Thr Gly Thr Arg Ser Pro
145                 150                 155                 160

Gln Pro Gly His Pro Gly Glu Asp Ile Ala Trp Glu Gly Arg Arg Glu
                165                 170                 175

Ala Ser Pro Arg Met Ser Met Cys Gly Glu Lys Arg Glu Gly Ser Gly
            180                 185                 190

Ser Glu Trp Ala Ala Ser Glu Gly Cys Pro Ser Leu Gly Cys Pro Ser
        195                 200                 205

Val Val Pro Ser Pro Cys Ser Ser Glu Lys Thr Phe Asp Phe Lys Gly
    210                 215                 220

Leu Arg Arg Met Ser Arg Thr Phe Ser Glu Cys Ser Tyr Pro Glu Thr
225                 230                 235                 240
```

-continued

| | | | | | | | | | | | | | | |
|---|---|---|---|---|---|---|---|---|---|---|---|---|---|---|
| Glu | Glu | Glu | Gly | Glu | Ala | Leu | Pro | Val | Arg | Asp | Ser | Phe | Tyr | Arg | Leu |
| | | | | 245 | | | | 250 | | | | | | 255 | |
| Glu | Lys | Arg | Leu | Gly | Arg | Ser | Glu | Pro | Ser | Ala | Phe | Leu | Arg | Gly | His |
| | | | 260 | | | | 265 | | | | | | 270 | | |
| Gly | Ser | Arg | Lys | Glu | Ser | Ser | Ala | Val | Leu | Ser | Arg | Ile | Gln | Lys | Ile |
| | | 275 | | | | | 280 | | | | | 285 | | | |
| Glu | Gln | Val | Leu | Lys | Glu | Gln | Pro | Gly | Arg | Gly | Leu | Pro | Gln | Leu | Pro |
| | 290 | | | | | 295 | | | | | 300 | | | | |
| Ser | Ser | Cys | Tyr | Ser | Val | Asp | Arg | Gly | Lys | Arg | Lys | Thr | Gly | Thr | Leu |
| 305 | | | | | 310 | | | | | 315 | | | | | 320 |
| Gly | Ser | Leu | Glu | Glu | Pro | Ala | Gly | Gly | Ala | Ser | Val | Ser | Ala | Gly | Ser |
| | | | | 325 | | | | | 330 | | | | | 335 | |
| Arg | Ala | Val | Gly | Val | Ala | Gly | Val | Ala | Gly | Glu | Ala | Gly | Pro | Pro | Pro |
| | | | 340 | | | | | 345 | | | | | 350 | | |
| Glu | Arg | Glu | Gly | Ser | Gly | Ser | Thr | Lys | Pro | Gly | Thr | Pro | Gly | Asn | Ser |
| | | 355 | | | | | 360 | | | | | 365 | | | |
| Pro | Ser | Ser | Gln | Arg | Leu | Pro | Ser | Lys | Ser | Ser | Leu | Asp | Pro | Ala | Val |
| | 370 | | | | | 375 | | | | | 380 | | | | |
| Asn | Pro | Val | Pro | Lys | Pro | Lys | Arg | Thr | Phe | Glu | Tyr | Glu | Ala | Glu | Lys |
| 385 | | | | | 390 | | | | | 395 | | | | | 400 |
| Asn | Pro | Lys | Ser | Lys | Pro | Ser | Asn | Gly | Leu | Pro | Pro | Ser | Pro | Thr | Pro |
| | | | | 405 | | | | | 410 | | | | | 415 | |
| Ala | Ala | Pro | Pro | Pro | Leu | Pro | Ser | Thr | Pro | Ala | Pro | Pro | Val | Thr | Arg |
| | | | 420 | | | | | 425 | | | | | 430 | | |
| Arg | Pro | Lys | Lys | Asp | Met | Arg | Gly | His | Arg | Lys | Ser | Gln | Ser | Arg | Lys |
| | | 435 | | | | | 440 | | | | | 445 | | | |
| Ser | Phe | Glu | Phe | Glu | Asp | Ala | Ser | Ser | Leu | Gln | Ser | Leu | Tyr | Pro | Ser |
| | 450 | | | | | 455 | | | | | 460 | | | | |
| Ser | Pro | Thr | Glu | Asn | Gly | Thr | Glu | Asn | Gln | Pro | Lys | Phe | Gly | Ser | Lys |
| 465 | | | | | 470 | | | | | 475 | | | | | 480 |
| Ser | Thr | Leu | Glu | Glu | Asn | Ala | Tyr | Glu | Asp | Ile | Val | Gly | Asp | Leu | Pro |
| | | | | 485 | | | | 490 | | | | | | 495 | |
| Lys | Glu | Asn | Pro | Tyr | Glu | Asp | Val | Asp | Leu | Lys | Ser | Arg | Arg | Ala | Gly |
| | | | 500 | | | | | 505 | | | | | 510 | | |
| Arg | Lys | Ser | Gln | Gln | Leu | Ser | Glu | Asn | Ser | Leu | Asp | Ser | Leu | His | Arg |
| | | 515 | | | | | 520 | | | | | 525 | | | |
| Met | Trp | Ser | Pro | Gln | Asp | Arg | Lys | Tyr | Asn | Ser | Pro | Pro | Thr | Gln | Leu |
| | 530 | | | | | 535 | | | | | 540 | | | | |
| Ser | Leu | Lys | Pro | Asn | Ser | Gln | Ser | Leu | Arg | Ser | Gly | Asn | Trp | Ser | Glu |
| 545 | | | | | 550 | | | | | 555 | | | | | 560 |
| Arg | Lys | Ser | His | Arg | Leu | Pro | Arg | Leu | Pro | Lys | Arg | His | Ser | His | Asp |
| | | | | 565 | | | | | 570 | | | | | 575 | |
| Asp | Met | Leu | Leu | Leu | Ala | Gln | Leu | Ser | Leu | Pro | Ser | Ser | Pro | Ser | Ser |
| | | | 580 | | | | | 585 | | | | | 590 | | |
| Leu | Asn | Glu | Asp | Ser | Leu | Ser | Thr | Thr | Ser | Glu | Leu | Leu | Ser | Ser | Arg |
| | | 595 | | | | | 600 | | | | | 605 | | | |
| Arg | Ala | Arg | Arg | Ile | Pro | Lys | Leu | Val | Gln | Arg | Ile | Asn | Ser | Ile | Tyr |
| | 610 | | | | | 615 | | | | | 620 | | | | |
| Asn | Ala | Lys | Arg | Gly | Lys | Lys | Arg | Leu | Lys | Lys | Leu | Ser | Met | Ser | Ser |
| 625 | | | | | 630 | | | | | 635 | | | | | 640 |
| Ile | Glu | Thr | Ala | Ser | Leu | Arg | Asp | Glu | Asn | Ser | Glu | Ser | Glu | Ser | Asp |
| | | | | 645 | | | | 650 | | | | | | 655 | |
| Ser | Asp | Asp | Arg | Phe | Lys | Ala | His | Thr | Gln | Arg | Leu | Val | His | Ile | Gln |
| | | | 660 | | | | | 665 | | | | | 670 | | |

| | | | | | | | | | | | | | | |
|---|---|---|---|---|---|---|---|---|---|---|---|---|---|---|
|Ser|Met|Leu|Lys|Arg|Ala|Pro|Ser|Tyr|Arg|Thr|Leu|Glu|Leu|Glu|Leu|
| | |675| | | |680| | | |685| | | | |
|Leu|Glu|Trp|Gln|Glu|Arg|Glu|Leu|Phe|Glu|Tyr|Phe|Val|Val|Val|Ser|
| |690| | | | |695| | | |700| | | | |
|Leu|Lys|Lys|Lys|Pro|Ser|Arg|Asn|Thr|Tyr|Leu|Pro|Glu|Val|Ser|Tyr|
|705| | | | |710| | | |715| | | | |720|
|Gln|Phe|Pro|Lys|Leu|Asp|Arg|Pro|Thr|Lys|Gln|Met|Arg|Glu|Ala|Glu|
| | | |725| | | |730| | | |735| | | |
|Glu|Arg|Leu|Lys|Ala|Ile|Pro|Gln|Phe|Cys|Phe|Pro|Asp|Ala|Lys|Asp|
| | |740| | | |745| | | |750| | | | |
|Trp|Leu|Pro|Val|Ser|Glu|Tyr|Ser|Ser|Glu|Thr|Phe|Ser|Phe|Met|Leu|
| | |755| | | |760| | | |765| | | | |
|Thr|Gly|Glu|Asp|Gly|Ser|Arg|Arg|Phe|Gly|Tyr|Cys|Arg|Arg|Leu|Leu|
| |770| | | | |775| | | |780| | | | |
|Pro|Ser|Gly|Lys|Gly|Pro|Arg|Leu|Pro|Glu|Val|Tyr|Cys|Val|Ile|Ser|
|785| | | | |790| | | |795| | | | |800|
|Arg|Leu|Gly|Cys|Phe|Gly|Leu|Phe|Ser|Lys|Val|Leu|Asp|Glu|Val|Glu|
| | | |805| | | |810| | | |815| | | |
|Arg|Arg|Arg|Gly|Ile|Ser|Ala|Ala|Leu|Val|Tyr|Pro|Phe|Met|Arg|Ser|
| | |820| | | |825| | | |830| | | | |
|Leu|Met|Glu|Ser|Pro|Phe|Pro|Ala|Pro|Gly|Lys|Thr|Ile|Lys|Val|Lys|
| |835| | | | |840| | | |845| | | | |
|Thr|Phe|Leu|Pro|Gly|Ala|Gly|Asn|Glu|Val|Leu|Glu|Leu|Arg|Arg|Pro|
|850| | | | |855| | | |860| | | | | |
|Met|Asp|Ser|Arg|Leu|Glu|His|Val|Asp|Phe|Glu|Cys|Leu|Phe|Thr|Cys|
|865| | | |870| | | |875| | | |880| | |
|Leu|Ser|Val|Arg|Gln|Leu|Ile|Arg|Ile|Phe|Ala|Ser|Leu|Leu|Leu|Glu|
| | | |885| | | |890| | | |895| | | |
|Arg|Arg|Val|Ile|Phe|Val|Ala|Asp|Lys|Leu|Ser|Thr|Leu|Ser|Ser|Cys|
| | |900| | | |905| | | |910| | | | |
|Ser|His|Ala|Val|Val|Ala|Leu|Leu|Tyr|Pro|Phe|Ser|Trp|Gln|His|Thr|
| |915| | | | |920| | | |925| | | | |
|Phe|Ile|Pro|Val|Leu|Pro|Ala|Ser|Met|Ile|Asp|Ile|Val|Cys|Cys|Pro|
|930| | | | |935| | | |940| | | | | |
|Thr|Pro|Phe|Leu|Val|Gly|Leu|Leu|Ser|Ser|Ser|Leu|Pro|Lys|Leu|Lys|
|945| | | | |950| | | |955| | | |960| |
|Glu|Leu|Pro|Val|Glu|Glu|Ala|Leu|Met|Val|Asn|Leu|Gly|Ser|Asp|Arg|
| | | |965| | | |970| | | |975| | | |
|Phe|Ile|Arg|Gln|Met|Asp|Asp|Glu|Asp|Thr|Leu|Leu|Pro|Arg|Lys|Leu|
| | |980| | | |985| | | |990| | | | |
|Gln|Ala|Ala|Leu|Glu|Gln|Ala|Leu|Glu|Arg|Lys|Asn|Glu|Leu|Ile|Ser|
| | |995| | | |1000| | | |1005| | | | |
|Gln|Asp|Ser|Asp|Ser|Asp|Ser|Asp|Asp|Glu|Cys|Asn|Thr|Leu|Asn|Gly|
| |1010| | | | |1015| | | |1020| | | | |
|Leu|Val|Ser|Glu|Val|Phe|Ile|Arg|Phe|Phe|Val|Glu|Thr|Val|Gly|His|
|1025| | | | |1030| | | |1035| | | | |1040|
|Tyr|Ser|Leu|Phe|Leu|Thr|Gln|Ser|Glu|Lys|Gly|Glu|Arg|Ala|Phe|Gln|
| | | |1045| | | |1050| | | |1055| | | |
|Arg|Glu|Ala|Phe|Arg|Lys|Ser|Val|Ala|Ser|Lys|Ser|Ile|Arg|Arg|Phe|
| | |1060| | | |1065| | | |1070| | | | |
|Leu|Glu|Val|Phe|Met|Glu|Ser|Gln|Met|Phe|Ala|Gly|Phe|Ile|Gln|Asp|
| | |1075| | | |1080| | | |1085| | | | |
|Arg|Glu|Leu|Arg|Lys|Cys|Arg|Ala|Lys|Gly|Leu|Phe|Glu|Gln|Arg|Val|

-continued

```
          1090                    1095                    1100
Glu  Gln  Tyr  Leu  Glu  Glu  Leu  Pro  Asp  Thr  Glu  Gln  Ser  Gly  Met  Asn
1105                     1110                    1115                    1120

Lys  Phe  Leu  Arg  Gly  Leu  Gly  Asn  Lys  Met  Lys  Phe  Leu  His  Lys  Lys
                    1125                    1130                    1135

Asn
```

( 2 ) INFORMATION FOR SEQ ID NO:3:

( i ) SEQUENCE CHARACTERISTICS:
      ( A ) LENGTH: 3266 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| TATTTAGCTG | GGCCTGTAGT | CCCAGCTACT | CAGGAGGCTG | AGGCAGGAGA | ATTGCTTGAA | 60 |
| TCCAGGAGGT | GGAGGTTGCA | GTGAGCGGAG | TTGTGCCACT | GCACTCCAGC | CTGGGAGTGA | 120 |
| CACTCTGTCT | CAAAATAAAT | AAATAAATAA | AAATTTAAAA | ATTTTTTTAA | AAAAAGGAAA | 180 |
| CAAAAACTTT | TCCTCTCTGC | ATAAATAAT | TTCTTAGTAA | GTCCTACAAC | AACAGGATGG | 240 |
| GTTATTGGCA | ACATGTTACA | TATTGTTTTG | GTCAAAGAAT | CCATCCCAAG | CAGTGGTTTC | 300 |
| TCTAGAGTGG | TCATTTGGAC | ATTGATTAAG | CCACCTTAAA | TGTCAGGTGC | TCACAGGAGG | 360 |
| GCAGTGAAGG | AAAATCCCCG | TTCTGGTTTG | TCCTCCAATA | AGTCCTGAAT | CCCTGGGGTA | 420 |
| TTTCCTTCCG | TATGTATGAG | GAAGCAGTTG | AGAGGAAACC | GAGAAATGAA | CTCCCGATTG | 480 |
| CCTTCAGAGG | GACAGGAACG | CAGGCCCATC | CTCAGCCCAG | GAGAAGAAAG | GAGGAAGAAA | 540 |
| AACCAGAGCT | GCTGACTTTT | CCATAGAGCA | CCAGGGTTTA | GAAAGGAAAA | CTGCCCCTCA | 600 |
| CTTGTTCCCA | TCACAGCCTC | AATGCTTCTG | TGTCTCACAC | TTCTAGGTGT | TCTGTGGGCC | 660 |
| CATCAGGCCC | TTGTGAAGAA | ATCTAGCCCA | ACAGCTGGAA | TGAGCTGGGT | ACAGCAGTTC | 720 |
| CAAGAGGCCC | CTCCTGTGTA | CCAGCCATGG | TCATTGTCAG | CCAACAAAGC | CCCTGACTGC | 780 |
| CCAGCTTTGG | TGCCCTGGCC | TGGCCTGACC | TTAGTGGCCC | CTAAGAGAGC | CTGGACCATG | 840 |
| AGGTTTCTTT | TCCTGAAGGT | TCTACCCTCT | AATTCAGGGC | TGAGCTTCCT | CTTTGCCACC | 900 |
| CTGCCCCTCC | ACAGGCCAGC | TCCCGTGGGG | CTGTGAATAC | AGCTATTGTT | TCCTGTGGTT | 960 |
| GCAGCTGCCT | CTGAGCACAT | TCCAGGACCA | TTCTGGGAGG | GACGATCCCA | AGGTCTTGTT | 1020 |
| CTTGGCCTGG | CCGGGTATTC | AAGTTCTGCC | AATCTGGGGT | CTTGGAAAAG | ATGTCCTTCC | 1080 |
| TGTTCTGCCT | GGGGTCTGCC | TCTGGCTGGA | GAGGGAGGG | GTAGGTCCAG | CCAGCTCATG | 1140 |
| ATCCGTTGCT | GATGTTTTAG | GTTTTCCACA | AGTTCTTTGT | CCCTCTTGCC | TAGTTCTGAT | 1200 |
| GTGGGGTGGG | AGAGGGTACC | CACGATCTGC | ATTCACTGGC | CCTAGGGGTT | TACAAAACCT | 1260 |
| ACTGCCTCCT | CAGCCACGGG | CCCACTGATG | TGCCCCCAA | ACCCGAGACA | GCCCTTTTCA | 1320 |
| GATCTTTGTC | AGATGACTGT | CCTGCGGGTT | GCTGCATACC | TTCCTGGCTG | TTTGCAGGTA | 1380 |
| CATTTCCCTA | AGAGAGTAGC | ATTGTTGTCC | TTGAGGCGCT | ACGCAGTGGG | AAAGCGGGGA | 1440 |
| CTTTACCAGT | CTGCAGGGTC | CCTGAACCCC | ATTAGCATTT | TTGTTGCACT | GGGAGGTTTA | 1500 |
| CGATCAAAGG | CTGTCCTGAG | CCTCCAGCGA | GCTCTAAGTT | CCTGGGCCTG | GCTCAGGTA | 1560 |
| CTCTGTCTCT | CTGTCTGCCC | ATCAGTACCC | TCTCCAGCTG | CTCCCACGCG | GTGGTGGCCT | 1620 |
| TGCTCTACCC | CTTCTCCTGG | CAGCACACCT | TCATTCCTGT | CCTCCCGGCC | TCCATGATTG | 1680 |
| ACATCGTCTG | CTGTCCCACC | CCCTTCCTGG | TTGGCCTGCT | CTCCAGCTCC | CTCCCCAAAC | 1740 |

| | | | | | |
|---|---|---|---|---|---|
| TGAAGGAGCT | GCCTGTGGAG | GAGGTGGGCC | ACCGGGGGAA | CCAGCTGGGG | GGAAGGGTGG | 1800 |
| AGGGGGAAGC | AGGTGCTGGG | ATCTTACTTG | TGGCCCCTCG | GCCTCTTTAC | CAGGCTCTTA | 1860 |
| TCCTTTCTCC | CTGGGAGGTC | TATCCCCGGC | TGGAGTACTT | CCTGTTAGCT | GACCCTGGGA | 1920 |
| ACCTGGGAGG | TCTGGAGGCC | TGGCAGAGGG | CATTGCGGGA | CTCATGCCCT | GAGCCACTCT | 1980 |
| GCTAATGACT | CCTTTTCTCA | GGCGCTGATG | GTGAATCTGG | GATCTGACCG | ATTCATCCGA | 2040 |
| CAGATGGACG | ACGAAGACAC | GTTGTTACCT | AGGAAGTTAC | AGGCAGCTCT | GGAGCAGGCT | 2100 |
| CTGGAGAGGA | AGAATGAGCT | GATCTCCCAG | GACTCTGACA | GCGACTCCGA | CGATGAATGT | 2160 |
| AATACCCTCA | ATGGGCTGGT | GTCGGAGGTG | TTTATCCGGT | TCTTTGTGGA | GACCGTTGGG | 2220 |
| CACTACTCCC | TCTTTCTGAC | ACAGAGTGAG | AAGGGAGAGA | GGGCCTTTCA | GCGAGAGGCC | 2280 |
| TTCCGCAAAT | CTGTGGCCTC | CAAAAGCATC | CGCCGCTTTC | TTGAGGTTTT | TATGGAGTCT | 2340 |
| CAGATGTTTG | CTGGCTTCAT | CCAAGACAGG | GAGCTAAGAA | AGTGTCGGGC | AAAGGGCCTT | 2400 |
| TTTGAGCAGC | GAGTGGAGCA | GTACTTAGAA | GAACTCCCAG | ACACTGAGCA | GAGTGGAATG | 2460 |
| AATAAGTTTC | TCCGAGGTTT | GGGCAACAAA | ATGAAGTTTC | TCCACAAGAA | GAATTAAGCC | 2520 |
| TCCTTCTCAG | TAGCAGAGTC | CAGTGCCTTG | CAGAGCCTGA | AGCCTGGGGA | GAAGGCCCAG | 2580 |
| CCTGGGACCC | TCTGGGCTGC | TGTGGCTCCT | CTGCCCCAC | AGATCCTATC | CTCCAAGCCA | 2640 |
| GCCCACCTCT | GCCTTCATCA | TATCCCAGGA | TACTGTTTGT | AAATAATCTG | CTGTAAGCTT | 2700 |
| TCTTAACTGT | TTTTTGTAAC | AAGCAAAGAG | AATATGGCAA | ATATTTGTAT | ATTCCCAAGG | 2760 |
| GGCCGGGTGC | TTTCCTGTCC | TGCCAGAGCA | TGGATGAAGT | TTCGCTGGGT | GCTCGTGACT | 2820 |
| GGCCAGTTTT | GTGCAGCTGA | CTGTCTCAGC | CAAACCACTG | ATCTTCCCTG | GAGGCCTTCG | 2880 |
| GCCTGCCTGC | CTGCCTGCCT | GAGGTCCCCG | CTGCCAGTCC | CGGGCCCTGG | AGAGCAGATG | 2940 |
| CTGTCTTGTT | ATGTACAGGA | GGACCTTTTA | AAAAAATCAA | GTTTCTATTT | TTTGCTGGTA | 3000 |
| GTCCGCATAC | CCATACCCTC | TGTTTTTGAA | AGGCAAAGGC | CAATCAGTCC | CCATTTGTGG | 3060 |
| CATGGCACCA | GGGTCTTAGG | CCTAGTCCTC | TCATTCCTCC | CACCCTCCGA | GATGGTCAGT | 3120 |
| GTGTCATGGG | AAGCCCACCC | CCAGCTCTGC | CAGTGCTCTC | TGGGCCTGGC | TCCCAGTCAG | 3180 |
| TGGTGGCCAC | GATGCGGTAC | AGGGCATCCC | TCCTTCCCAT | CTACGGGTGT | TGTCAATAAA | 3240 |
| CAATGTACAG | TTGTTTGGGC | CCAGAG | | | | 3266 |

( 2 ) INFORMATION FOR SEQ ID NO:4:

( i ) SEQUENCE CHARACTERISTICS:
    ( A ) LENGTH: 168 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

| | | | | | |
|---|---|---|---|---|---|
| CTGAACACTT | CCTCCTTGCT | AATCACTGTT | CCGTTCCGAG | GTTGCCTCAG | TGAACAACAC | 60 |
| AAAACCCTGC | CCTAAAAGAC | TTGTTGAACG | GCATCGTAGG | TGAGAAGGGG | GCCTGGCGAA | 120 |
| GCCCTGCTCC | CTACGGTTCT | GTGAGTTCCT | CCATGCCCAC | CCTCCAAA | | 168 |

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

GACTGGCAGC GGGGACCTCA 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AGCCAAACCA CTGATCTTCC 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

AAAAGCTCCT CGAGGAACTG 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CGCATATGGT GCACTCTCAG 20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TCACTGCATT CTAGTTGTGG 20

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
CCGGATCCGG TGGTGGTGCA AATC                                                                      24
```

HTS-1 GENE, A HUMAN TUMOR SUPPRESSOR GENE

This is a Continuation of application Ser. No. 07/916,762, filed Jul. 17, 1992, now abandoned.

BACKGROUND OF THE INVENTION

Chromosome 11 contains genes which can suppress the tumorigenicity of HeLa cells in nude mice. Suppression of tumorigenicity in HeLa cells was first demonstrated in studies of somatic cell hybrids of HeLa cells with normal human fibroblasts. See, Klinger, *Cytogenet. Cell Genet.*, 27:254–266 (1980) and Stanbridge, *Nature*, 260:17–20 (1976). These hybrid cell lines, unlike HeLa, were non-tumorigenic, but retained other properties of transformed cells such as immortalization and the ability to grow in soft agar. See, Stanbridge, et al., *Science*, 215:252–259 (1982). The non-tumorigenic hybrids gave rise to rare segregants which had regained the property of tumorigenicity. Karyotype and RFLP analysis of such segregants demonstrated a loss of one copy of chromosome 11 relative to the non-tumorigenic cell lines. See, Srivatsan, et al., *Cancer Res.* 46:6174–6179 (1986) and Kaelbling, et al., *Cytogenet. Cell Genet.*, 42:65–70 (1986). Direct functional evidence for the existence of a chromosome 11 HeLa tumor suppressor came with the demonstration that microcell mediated transfer of chromosome 11 to HeLa or a tumorigenic segregant line resulted in partial or complete suppression of tumorigenicity. See, Saxon, et al., *EMBO J.*, 5:3461–3466 (1986). Tumor suppression mediated by chromosome 11 transfer has also been demonstrated in a cell line derived from a Wilms' tumor (see, Weissmann, et al., *Science*, 236:175–180 (1980)), in the cervical carcinoma cell line SiHa (see, Koi, et al., *Mol. Carcinogen.*, 2:12–21 (1989)), and in a rhabdomyosarcoma cell line (see, Oshimura, et al., *J. Cell. Biochem.*, 42:135–142 (1990)).

The specific chromosome 11 gene or genes responsible for tumor suppression in the HeLa-fibroblast system have not been identified. Comparison of proteins and RNA species expressed by hybrid cell lines has revealed that extremely few genes show differential expression between the tumorigenic and non-tumorigenic hybrids. For example, when $1.2 \times 10^5$ clones from a subtracted cDNA library were screened, only one differentially expressed gene was identified. See, Dowdy, et al., *Nuc. Acids Res.*, 19:5763–5769 (1991). This gene was expressed at only 2–4 fold higher levels in the non-tumorigenic hybrids than in the tumorigenic segregants. In the HeLa/fibroblast system, one gene which displays marked differential expression has been characterized: that for intestinal alkaline phosphatase (IAP). Both HeLa and the tumorigenic segregants express high levels of this enzyme, whereas virtually no RNA, protein, or enzyme activity is detectable in the suppressed hybrids. See, Latham, et al., *Proc. Natl. Acad. Sci. USA*, 87:1263–1267 (1990). Although the IAP gene may prove to be a target of the tumor suppressor gene, it does not map to chromosome 11 and does not by itself affect tumorigenicity upon transfection. See, Latham, et at., *Cancer Research*, 52:616–622 (1992).

A gene which is associated with tumor suppression and is localized on chromosome 11 has now been identified. The identification, localization and sequence of a gene which demonstrates differential expression in a manner that correlates with tumorigenicity suggests that this gene could potentially be used for gene therapy in cancers deleted or altered in their expression of the gene. Furthermore, a gene which is localized on chromosome 11p15, with identified polymorphisms, could be used for analysis of tumor DNA for loss of heterozygosity at chromosome 11p15. This region of chromosome 11 shows frequent loss of heterozygosity (LOH) in many human malignancies. See, Junien, et al., *Genomics*, 12:620–625 (1992). Thus, the determination of LOH at chromosome 11p15 may be useful in predicting the prognosis of that tumor.

SUMMARY OF THE INVENTION

This invention provides for a substantially purified nucleic acid having a sequence substantially identical to a nucleic acid of Sequence I.D. No. 1. This invention further provides for a substantially purified nucleic acid encoding the polypeptide of Sequence I.D. No. 2. This invention also provides for nucleic acid probes that are subsequences of the HTS1 gene and have at least 12 nucleotides, said probes specific for binding to HTS1. By specific it is meant that the probe does not substantially bind to other sequences in the human genome. The preferred probes are:

(a) bases 3570 to 4205 of Seq. I.D. No. 1;

(b) bases 305 to 2698 of Seq. I.D. No. 3; and (c) Seq. I.D. No. 4.

The present invention further provides a substantially purified nucleic acid which is substantially identical to the nucleic acid of Sequence I.D. No. 1 and which is operably linked to a promoter, preferably when contained in an expression vector.

The present invention further provides a cell transformed or transfected with a nucleic acid having a sequence substantially identical to the nucleic acid of Seq. I.D. No. 1 and which may be operably linked to a promoter. The preferred cell is mammalian.

The present invention further provides a substantially purified polypeptide having an amino acid sequence substantially identical to a polypeptide of Sequence I.D. No. 2.

The present invention further provides a method of detecting the presence of HTS1 in a physiological specimen, using the steps comprising:

(i) contacting a nucleic acid probe which is complementary to a portion of the HTS1 gene with the specimen under conditions which allow said nucleic acid probe to anneal to complementary sequences in said sample; and (ii) detecting duplex formation between the nucleic acid probe and the complementary sequence.

The preferred nucleic acid probe of step (i) is a subsequence of the entire HTS1 gene, more preferably the probe corresponds to bases 3570 to 4205 of Sequence I.D. No. 1. The target nucleic acid of the specimen may be genomic DNA, mRNA or cDNA. Additionally, this method may be used to detect HTS1 polymorphisms by first digesting the specimen with an endonuclease restriction enzyme and then allowing the resulting nucleic acid fragments to anneal to the nucleic acid probe of step (i).

The present invention further provides a method of detecting HTS1 using PCR for amplification of the HTS1 gene or a portion thereof. Preferred is a PCR method using the following set of primers: GACTGGCAGCGGGGACCTCA (Seq. I.D. No. 5) and AGCCAAACCACTGATCTTCC (Seq. I.D. No. 6).

The present invention further provides a method for the detection of HTS1 in a physiological specimen, using immunoassays and the following steps:

(i) contacting the physiological specimen with a substantially purified immunoglobulin that specifically binds the polypeptide encoded by the HTS1 gene;

(ii) allowing the immunoglobulin to bind to the polypeptide;

(iii) removing immunoglobulin not bound to the polypeptide; and (iv) detecting the bound immunoglobulin. Any standard immunoassay may be used, however preferred modes include radioimmunoassays and ELISA.

The preferred physiological specimen for any methods of the present invention are, human tissue, blood, or cells grown in culture.

DETAILED DESCRIPTION

Definitions

Nucleic acids

The phrase "nucleic acid sequence" refers to a single or double-stranded polymer of deoxyribonucleotide or ribonucleotide bases read from the 5' to the 3' end. It includes both self-replicating plasmids, infectious polymers of DNA or RNA and non-functional DNA or RNA.

Nucleic acids, as used herein, may be DNA or RNA. Additionally, substantial nucleic acid sequence identity exists when a nucleic acid segment will hybridize under selective hybridization conditions, to a complement of another nucleic acid strand.

The term "complementary" means that one nucleic acid is identical to, or hybridizes selectively to, another nucleic acid. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, M. Kanehisa *Nucleic Acids Res.* 12:203 (1984), incorporated herein by reference.

"Isolated" or "substantially pure", when referring to nucleic acids, refer to those that have been purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. *Current Protocols in Molecular Biology*, Greene Publishing and Wiley-Interscience, New York (1987), incorporated herein by reference.

"Nucleic acid probes" may be DNA fragments prepared, for example, by PCR as discussed above, or synthesized by either the phosphoramidite method described by Beaucage and Carruthers, *Tetrahedron Lett.* 22:1859–1862 (1981), or by the triester method according to Matteucci, et al., *J. Am. Chem. Soc.*, 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific nucleic acid sequence is given, it is understood that the complementary strand is also identified and included. For the complementary strand will work equally well in situations where the target is a double stranded nucleic acid.

A nucleic acid probe is complementary to a target nucleic acid when it will anneal only to a single desired position on that target nucleic acid under conditions determined as described below. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

The term "promoter" refers to a region of DNA upstream from the structural gene and involved in recognition and binding RNA polymerase and other proteins to initiate transcription.

The term "operably linked" refers to functional linkage between a promoter and a second sequence, wherein the promoter sequence initiates transcription of RNA corresponding to the second sequence. Generally, operably linked means that the nucleic acid sequences being linked are contiguous and, where necessary to join two protein coding regions, contiguous and in reading frame.

Techniques for nucleic acid manipulation, such as subcloning nucleic acid sequences encoding polypeptides into expression vectors, labelling probes, DNA hybridization, and so on are described generally, for example in Sambrook et al. (1989) op. cit., or Ausubel et all, ed. (1987) op. cit., both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

Proteins

The terms "peptide", "polypeptide" or "protein" are used interchangeably herein. The term "substantial identity", when referring to polypeptides, indicates that the polypeptide or protein in question is at least about 70% identical to an entire naturally occurring protein (native) or a portion thereof, and preferably at least about 95% identical.

As used herein, the terms "isolated" and "substantially pure" are used interchangeably and describe a protein that has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially purified protein will typically comprise over about 85 to 90% of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification utilized.

A polypeptide is substantially free of naturally-associated components when it is separated from the native contaminants which accompany it in its natural state. Thus, a polypeptide which is chemically synthesized or synthesized in a cellular system different from the cell from which it naturally originates will be substantially free from its naturally-associated components.

The proteins of this invention may be purified to substantial homogeneity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

Immunoglobulins

As used herein, "immunoglobulin" refers to molecules which have specific immunoreactive activity. Antibodies are typically tetramers of immunoglobulin molecules. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains. Heavy chain types are alpha, gamma, delta, epsilon and mu. The carboxy terminal portions of immunoglobulin heavy and light chains are constant regions, while the amino terminal portions are encoded by the myriad immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains (e.g., Huston, et al., *Proc. Nat. Acad. Sci. U.S.A.*, 85:5879–5883 (1988) and Bird, et al., *Science* 242:423–426 (1988), which are incorporated herein by reference). (See generally, Hood, et al., "Immunology", Benjamin, N.Y., 2nd ed. (1984), and Hunkapiller and Hood, *Nature*, 323:15–16 (1986), which are incorporated herein by reference). Single-chain antibodies, in which genes for a heavy chain and a light chain are combined into a single coding sequence, may also be used.

"Monoclonal antibodies" may be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.* 6:511–519 (1976), incorporated herein by reference). Alternative methods of immortalization include transformation with Epstein Bart Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

DESCRIPTION OF THE INVENTION

An isolated nucleic acid sequence, termed HTS1, and the novel polypeptide which it encodes are described herein.

The nucleic acid compositions of this invention, whether RNA, cDNA, genomic DNA, or a hybrid of the various combinations, may be isolated from natural sources or may be synthesized in vitro. The preferred natural source is a HeLa cell line. The nucleic acids claimed may be present in transformed or transfected whole cells, in a transformed or transfected cell lysate, or in a partially purified or substantially pure form.

Nucleic acid probes are also included in the claimed invention. Such probes are useful for detecting the presence of HTS1 in physiological samples, and as primers for gene amplification. The nucleic acid probes will usually be at least about 20 nucleotides in length, more typically they will be more than 500 nucleotides in length.

A method of isolating HTS1 is also described herein. Briefly, the nucleic acid sequences can be isolated by probing a DNA library which is comprised of either genomic DNA or cDNA. Libraries may be either from commercial sources or prepared from mammalian tissue by techniques known to those skilled in the art. The preferred cDNA libraries are human cDNA libraries which are available from commercial sources.

The DNA libraries can be probed by plaque hybridization using nucleic acid probes of at least 20 base pairs which are complementary to unique sequences of the HTS1 gene. The preferred probes are: bases 3570 to 4205 of Seq. I.D. No.1, bases 305 to 2698 of Seq. I.D. No. 3, and Seq. I.D. No. 4. Additionally, the probes are labeled to facilitate isolation of the hybridized clones. Labeling can be by any of the techniques known to those skilled in the art, but typically the probes are labeled with $^{32}$P using terminal deoxynucleotidyltransferase. Alternatively and preferably the DNA encoding the polypeptide can be obtained using PCR.

Through the use of recombinant DNA techniques one may express the HTS1 gene in yeast, filamentous fungal, insect (especially employing baculoviral vectors), mammalian cells, and preferably in bacterial systems. For this purpose, the natural or synthetic nucleic acids included in the invention will typically be operably linked to a promoter (which is either constitutive or inducible), and may be incorporated into an expression vector.

The isolated nucleic acid sequences can then be inserted into a cloning vector suitable for replication and integration in either prokaryotes or eukaryotes. The cloning vectors contain transcription and translation terminators, initiation sequences, and promoters useful for regulation of the expression of the HTS1 gene. The vectors are comprised of expression cassettes containing at least one independent terminator sequence, sequences permitting replication of the plasmid in both eukaryotes and prokaryotes, i.e., shuttle vectors, and selection markers for both prokaryotic and eukaryotic systems. In a preferred embodiment of this invention, plasmid pGEX (Pharmacia, PL Biochemicals, Milwaukee, Wis.) is used as a vector for the subcloning and amplification of desired gene sequences. This bacterial expression plasmid expressed HTS1 as a fusion protein (glutathione) from a tac promoter.

Methods for the expression of cloned genes in bacteria are well known. To obtain high level expression of a cloned gene in a prokaryotic system, it is essential to construct expression vectors which contain, at a minimum, a strong promoter to direct mRNA transcription termination. The inclusion of selection markers in DNA vectors transformed in *E. coli* is also useful. Examples of such markers include genes specifying resistance to ampicillin, tetracycline, or chloramphenicol. See Sambrook for details concerning selection markers and promoters for use in *E. coli*.

It is expected that those of skill in the art are knowledgeable in the expression systems chosen for expression of the HTS1 gene and no attempt to describe in detail the various methods known for the expression of proteins in eukaryotes will be made.

Suitable eukaryote hosts may include plant cells, insect cells, mammalian cells, yeast, filamentous fungi, or preferably, bacteria (e.g., *E. coli* or *B. subtilis*).

The protein encoded by the HTS1 gene which is produced by recombinant DNA technology may be purified by standard techniques well known to those of skill in the art. Alternatively and preferably, fusion proteins produced by the above method may be purified by a combination of sonication and affinity chromatography. Subsequent digestion of the fusion protein with an appropriate proteolytic enzyme releases the desired polypeptide.

Alternatively, the polymerase chain reaction (PCR) is useful for isolating the HTS1 gene from physiological samples. The sequence of PCR primers, as for probes, may be based on any region of the HTS1 gene, for purposes discussed above, or may be based upon any other claimed nucleic acid. Exact complementarity to the nucleic acids being tested for is not required, but rather substantial complementarity is sufficient.

Using the sequences provided herein, those of skill may use polymerase chain reaction technology (PCR) to amplify nucleic acid sequences of the HTS1 gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of HTS1 in physiological samples, for nucleic acid sequencing, or for other purposes. Appropriate primers and probes for identifying HTS1 from alternative mammalian tissues are generated from comparisons of the sequences provided herein. For a general overview of PCR see *PCR Protocols: A Guide to Methods and Applications*. (Innis, M, Gelfand, D., Sninsky, J. and White, T., eds.), Academic Press, San Diego (1990), incorporated herein by reference.

In summary, the HTS1 gene can prepared by probing or amplifying select regions of a mixed cDNA or genomic pool using the probes and primers generated from the sequences provided herein.

The HTS1 gene appears in the human population in various forms. By following the methods disclosed herein, one can evaluate the polymorphisms. One can then determine the significance of a particular deletion for a patient. Characterization of the alleles is done by comparison with non-cancerous cells preferably from DNA extracted from peripheral blood cells. More specifically in individuals that are heterozygous for the allele, the loss of one allele is revealed by methods described herein. Importantly where two alleles are present in the normal cells, determining the loss of one allele is expected to provide information regarding the prognosis of the cancer or its sensitivity to various therapeutic alternatives.

The present invention also provides methods for detecting the presence or absence of HTS1 in a physiological specimen.

One method involves a Southern transfer and is well known to those of skill in the art. Briefly, the digested genomic DNA is run on agarose slab gels in buffer and transferred to membranes. Hybridization is carried out using the probes discussed above. Visualization of the hybridized portions allows the qualitative determination of the presence or absence of HTS1.

Similarly, a Northern transfer may be used for the detection of HTS1 in samples of RNA. This procedure is also well known in the art. See, Maniatis, et al., *Molecular Cloning: A laboratory manual*, Cold Spring Harbor Laboratory, Cold Spring Harbor, N.Y. (1982). In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the HTS1 transcript.

An alternative means for determining the level of expression of the HTS1 gene is in situ hybridization. In an in situ hybridization cells are fixed to a solid support, typically a glass slide. If DNA is to be probed the cells are denatured with heat or alkali. The cells are then contacted with a hybridization solution at a moderate temperature to permit annealing of HTS1 specific probes that are labelled. The probes are preferrably labelled with radioisotopes or fluorescent reporters. In situ hybridization assays are well known and are generally described in Angerer, et al., *Methods Enzymol.*, 152:649–660 (1987).

In addition to the detection of HTS1 using nucleic acid hybridization technology, one can use immunoassays to detect the HTS1 gene product. Immunoassays can be used to qualititatively and quantitatively analyze the HTS1 gene product. A general overview of the applicable technology can be found in Harlow and Lane, *Antibodies: A Laboratory Manual*, Cold Spring Harbor Pubs., N.Y. (1988). In brief the HTS1 gene product or a fragment thereof is expressed in transfected cells, preferably bacterial cells, and purified as generally described above and in the examples. The product is then injected into a mammal capable of producing antibodies. Either monoclonal or polyclonal antibodies specific for the gene product can be used in various immunoassays. Such assays include ELISA, competitive immunoassays, radioimmunoassays, western blots, indirect immunofluorescent assays and the like.

EXAMPLE 1

Isolation and Characterization of HTS1—A Tumor Suppressor Gene

1. Transfection of cDNA expression library and isolation of revertant clone F2.

The HTS1 gene was identified from a cDNA library by complementation of the tumorigenic cell line ESH 5L to restore a non-tumorigenic phenotype. A human fibroblast cDNA expression library estimated to contain $5 \times 10^6$ distinct cDNA species was obtained from Dr. Hiroto Okayama (Osaka University). This library was prepared in the pcD2 vector system. See, Chen, et al., *Mol. Cell. Biol.* 7:2745–2752 (1987). The library consisted of plasmids containing the neomycin resistance gene and a cDNA driven by separate copies of the SV40 early promoter. The tumorigenic segregant cell line ESH 5L was transfected with the cDNA expression library by a modified calcium phosphate precipitation method using a 5% $CO_2$ atmosphere. See, Chen, et al., *Mol. Cell. Biol.* 7:2745–2752 (1987). Transfected cells were trypsinized one day after removal of the precipitate, counted, and divided equally among nine 10 cm. diameter tissue culture plates. Selection in medium containing G418 (800 μg/mL) was begun 24 hrs. after plating. After three weeks of selection, each plate contained approximately 20–30 colonies of greater than 2 mm. in diameter plus numerous microscopic colonies. Colonies were screened for an altered morphology and candidate revertants were cloned. Twenty colonies which appeared "flat" microscopically were initially cloned, but none of these clones retained the altered morphology during continued passage in culture. The remaining cells were subjected to a modified adhesion selection procedure. See, Noda et al., *Proc. Natl. Acad. Sci. USA*, 86:162–166 (1989). After 24 days of selection in G418, cells were trypsinized, pelleted, resuspended in 10 mL of medium, and allowed to adhere to bacterial petri dishes (Falcon #1029) for one hour at 37° C. Medium and non-adherent cells were aspirated and the plates were washed gently with an additional 5 mL of medium. The cells which had adhered to the plates were removed by vigorous pipetting, reseeded into 10 cm tissue culture plates and allowed to grow into colonies. Candidate revertants were again identified morphologically. One clone maintained the flat morphology stably for several passages and was designated "F2."

2. Isolation of the integrated cDNA

For isolation of the integrated cDNA in the F2 cell line, two sequential PCR reactions using nested sets of primers derived from vector sequences were carried out. The PCR reactions were carried out in volumes of 0.100 mL, and contained 2.5 units AmpliTaq polymerase (Perkin-Elmer Cetus), salts and buffer as recommended by the manufacturer, and primers at a concentration of 0.2 µM. The first reaction contained F2 DNA (0.1 µg) and the following oligonucleotide primers: AAAAGCTCCTCGAGGAACTG (Seq. I.D. No. 7) and CGCATATGGTGCACTCTCAG (Seq. I.D. No. 8). The products of this reaction were purified away from excess primer on a Separose CL-4B spin column. The eluate from this column was ethanol precipitated and added to a second PCR reaction mixture containing the following primers: TCACTGCATTCTAGTTGTGG (Seq. I.D. No. 9) and CCGGATCCGGTGGTGGTGCAAATC (Seq. I.D. No. 10). The thermocycling parameters for both rounds of PCR were: one cycle of 94° C. for 90 sec/65° C. for 2 min/70° C. for 5 min; 30 cycles of 94° C. for 1 min/65° C. for 2 min/70° C. for 5 min; one cycle of 94° C. for 1 min/65° C. for 2 min/70° C. for 10 min. The products of the second PCR reaction were purified on an agarose gel, digested with BamH1, and subcloned into a vector consisting of the 3.0 kb BamH1 fragment of an Okayama-Berg cDNA. See, Okayama, et al., *Mol. Cell. Biol.*, 2:280–289 (1983) and Okayama, et al., *Methods Enzymol.*, 45:3–28 (1987).

3. DNA sequence analysis.

DNA sequences were determined with the Sequenase kit (U.S. Biochemical). The DNA sequence for HTS1 is given in Sequence I.D. No. 1. DNA and deduced amino acid sequences were searched against GenBank, EMBL, GenPept, PIR, and Swiss-Prot databases by using the BLAST network service at the NCBI. See, Altschul, et al., *J. Mol. Biol.*, 215:403–410 (1990).

EXAMPLE 2

Detection of the HTS1 Gene in a Physiological Specimen

1. DNA and RNA analysis.

Preparation of genomic DNA and poly-A selection of RNA followed standard methods. See, Maniatis, et al. *Molecular Cloning: A laboratory manual*, Cold Spring Harbor Laboratory, Cold Spring Harbor, N.Y., (1982). Whole cell RNA was prepared by the acid guanidinium-phenol-chloroform extraction method. See, Chomczynski, et al., *Anal. Biochem.*, 162:156–159 (1987). For Southern blots, digested genomic DNA was run on 1% agarose slab gels in Tris-acetate buffer and transferred to GeneScreen membranes (NEN) in 10× SSC. For Northern blots, RNA was separated on 1% agarose gels containing 6% formaldehyde in MOPS/acetate buffer. The gel was soaked for 30 min in 0.5M NaOH, then for 30 min in 0.5M Tris pH 7.4. RNA was transferred to GeneScreen membranes in 20×SSC. Membranes were crosslinked with a Stratalinker (Stratagene), prehybridized and hybridized in a solution containing 7%SDS/1%BSA/0.5M Sodium Phosphate, pH 7.2/1mM EDTA. See Church, et al., *Proc. Natl. Acad. Sci.*, 81:1991–1995 (1984). Washing produced a final stringency of 0.1×SSC/0.1%SDS at 65° C. The size of RNA species was estimated by comparison to a ladder of RNA markers (BRL, 0.24–9.5 kb).

EXAMPLE 3

Antibodies for the Detection of HTS1

Antiserum was raised against HTS1 proteins as follows: The portion of the HTS1 open reading frame extending from nucleotide 1722 to 2593 was subcloned into a pATH 22 vector. This bacterial expression plasmid using the trp/lac promoter expressed a trpE-HTS1 fusion protein of the predicted size in bacteria. The fusion protein was purified by SDS/PAGE electrophoresis, recovered by electroelution, and used as an antigen to immunize rabbits, following standard protocols. Immune serum was shown to contain HTS1 immunoreactivity in the following assays: (A) In an ELISA (enzyme linked immunosorbent assay) sera reacted with the purified antigen at titers of $1:10^3-1:10^5$ whereas preimmune serum was negative. (B) on Western blots, immune serum reacted specifically with purified antigen; preimmune serum did not. (C) In immunoprecipitations, the antisera was able to precipitate the purified antigen. The antisera therefore have utility in the detection and quantitation of HTS1 expression in human cells, derived either from tissue culture or from clinical specimens.

These antibodies have been applied to the detection of HTS1 proteins in several human cell lines and to the analysis of the cellular distribution and subcellar localization of the HTS1 proteins. On Western blots, normal (non-malignant) human epithelial cell primary cultures were found to contain immunoreactive proteins of apparent molecular masses of 68 and 175 kilodaltons. Analysis of malignant cells revealed several forms of the protein not detected in the primary cultures. Depending on the cell line, proteins of 134, 62 or 38 kilodaltons were detected in addition to the species noted in the benign cells.

The antibodies have been applied to the immunohistochemical detection of HTS1 proteins in frozen sections of human, mouse, and bovine tissues, following standard protocols. Preliminary experiments have demonstrated the utility of the current reagents in detection of the gene products in tissue. Initial results suggest tissue specific differential expression of HTS1 proteins. Levels of the protein also appear to be greater in more differentiated cell types relative to their less differentiated precursors (e.g.: higher levels in the superficial layers of skin than in the basal layer).

What is claimed is:

1. A purified nucleic acid having a sequence fully complementary to a nucleic acid of Sequence I.D. No. 1 said sequence binding specifically to sequence I.D. No. 1 and not to other human DNA sequences, when subject to 0.1× standard saline citrate buffer, 0.1% SDS at 65° C.

2. A purified nucleic acid of claim 1 encoding the polypeptide of Sequence I.D. No. 2.

3. A purified nucleic acid of claim 1 which has a sequence of Sequence I.D. No. 1.

4. A purified nucleic acid of claim 1 having at least 12 continuous nucleotides.

5. A subsequence of the nucleic acid of claim 4, comprising bases 3570 to 4205 of Seq. I.D. No. 1.

6. A purified nucleic acid of claim 1, wherein a promoter is operably linked to the nucleic acid.

7. A nucleic acid of claim 6, wherein the promoter and the nucleic acid are contained in an expression vector.

8. A cell transformed or transfected with a nucleic acid of claim 1.

9. A cell of claim 8, wherein the cell is mammalian.

10. A cell transformed or transfected with a nucleic acid of claim 6.

11. A cell of claim 10, wherein the cell is mammalian.

12. A method of detecting the presence of the human tumor suppressor 1 gene in a physiological specimen, said method comprising;
   (i) contacting a nucleic acid probe which is at least 12 continuous nucleotides in length and is specific for binding to human tumor suppressor 1 gene with said specimen under conditions which allow said nucleic acid probe to anneal to complementary sequences in said sample; and
   (ii) detecting duplex formation between said nucleic acid probe and said complementary sequences.

13. A method of claim 12, wherein the nucleic acid probe of step (i) is a subsequence of the entire human tumor suppressor 1 gene.

14. A method of claim 12, wherein the specimen further comprises mRNA and the nucleic acid probe of step (i) is annealed to said mRNA.

15. A method of claim 14, wherein the mRNA is reverse transcribed to cDNA prior to annealing of the nucleic acid probe in step (i).

16. A method of claim 12, comprising in step (i) a second nucleic acid probe, further comprising multiple nucleic acid probes wherein two of the nucleic acid probes are PCR primers and further comprising between steps (i) and (ii), amplification of the human tumor suppressor 1 gene or subsequence thereof using PCR.

17. A method of claim 16, wherein PCR is used with the following set of primers: GACTGGCAGCGGGGACCTCA (Seq. I.D. No. 5) and AGCCAAACCACTGATCTTCC (Seq. I.D. No. 6).

18. A method of claim 12, wherein said physiological specimen is a member selected from the group consisting of human tissue, blood, and cells grown in culture.

19. A method of claim 12, further comprising the step of digesting the human tumor suppressor 1 gene with an endonuclease restriction enzyme prior to step (i).

20. A method of claim 12, wherein the nucleic acid probe binds to an intron found within the human tumor suppressor 1 gene.

21. A method of claim 12, wherein the nucleic acid probe comprises bases 305 to 2698 of Seq. I.D. No. 3.

22. A method of claim 12, wherein the nucleic acid probe has a sequence of Seq. I.D. No. 4.

* * * * *